(12) United States Patent
Grier, Jr. et al.

(10) Patent No.: US 10,351,812 B2
(45) Date of Patent: Jul. 16, 2019

(54) DEVICE AND SYSTEM FOR CREATING AND MAINTAINING A LOCALIZED ENVIRONMENT FOR A CELL CULTURE PLATE

(71) Applicant: Axion BioSystems, Inc., Atlanta, GA (US)

(72) Inventors: Robert Dixon Grier, Jr., Atlanta, GA (US); David Ernest Irvine, Mint Hill, NC (US); James David Ross, Decatur, GA (US)

(73) Assignee: AXION BIOSYSTEMS, INC., Atlanta, GA (US)

( * ) Notice: Subject to any disclaimer, the term of this patent is extended or adjusted under 35 U.S.C. 154(b) by 509 days.

(21) Appl. No.: 14/838,575

(22) Filed: Aug. 28, 2015

(65) Prior Publication Data
US 2017/0058246 A1    Mar. 2, 2017

(51) Int. Cl.
*C12M 1/00* (2006.01)
*C12M 1/12* (2006.01)
*C12M 1/32* (2006.01)
*C12M 1/34* (2006.01)
*C12M 3/00* (2006.01)

(52) U.S. Cl.
CPC ............ *C12M 41/34* (2013.01); *C12M 23/04* (2013.01); *C12M 23/12* (2013.01); *C12M 23/40* (2013.01); *C12M 23/42* (2013.01); *C12M 23/44* (2013.01); *C12M 41/14* (2013.01)

(58) Field of Classification Search
CPC ...... C12M 41/34; C12M 23/04; C12M 23/12; C12M 23/40; C12M 23/42; C12M 23/44; C12M 41/14; C12M 23/38; G01N 35/028; G01N 35/04; G01N 2035/00356; G01N 2035/0403; G01N 2035/0477;
(Continued)

(56) References Cited

U.S. PATENT DOCUMENTS 4,301,252 A    11/1981  Baker et al.
4,572,427 A *  2/1986   Selfridge .................. A01C 1/02
                                                            165/146
(Continued)

FOREIGN PATENT DOCUMENTS

EP    0182926    6/1986
EP    2505635    10/2012
(Continued)

*Primary Examiner* — William H. Beisner
*Assistant Examiner* — Danielle B Henkel
(74) *Attorney, Agent, or Firm* — Meunier Carlin & Curfman LLC

(57) ABSTRACT

Systems and methods for creating a localized environment for a cell culture plate are described herein. An example system can include a dock shaped to receive the cell culture plate, and a gas distribution device positioned on the dock. The gas distribution device can include a frame including a plurality of sides connected to form an opening, an internal channel within the frame for directing a gas mixture within the gas distribution device, an inlet port in fluid communication with the internal channel for receiving the gas mixture, and a plurality of apertures in fluid communication with the internal channel. The plurality of apertures can be spaced apart from one another along the frame and configured to direct the gas mixture toward the opening.

18 Claims, 6 Drawing Sheets

(58) Field of Classification Search
CPC .............. B01L 9/523; B01L 2200/142; B01L 2300/041; B01L 2300/0829
See application file for complete search history.

(56) References Cited

U.S. PATENT DOCUMENTS

| | | | |
|---|---|---|---|
| 4,892,830 A | 1/1990 | Findley et al. | |
| 6,727,089 B2* | 4/2004 | Ho | C12M 41/12 356/244 |
| 6,878,177 B2 | 4/2005 | Lohr et al. | |
| 7,326,565 B2 | 2/2008 | Yokoi et al. | |
| 7,765,868 B2 | 8/2010 | Pirsch et al. | |
| 7,906,324 B2 | 3/2011 | Anderson et al. | |
| 8,187,868 B2 | 5/2012 | Kenney et al. | |
| 8,545,759 B2 | 10/2013 | Niazi | |
| 8,822,204 B2* | 9/2014 | Tsuchiya | G02B 21/30 359/395 |
| 2003/0092178 A1 | 5/2003 | Yerden | |
| 2003/0108450 A1* | 6/2003 | Mainquist | B01L 3/50853 422/400 |
| 2005/0276728 A1* | 12/2005 | Muller-Cohn | A01N 1/00 422/400 |
| 2006/0194193 A1* | 8/2006 | Tsuruta | C12M 29/10 435/4 |
| 2006/0275896 A1 | 12/2006 | Anderson et al. | |
| 2011/0129915 A1 | 6/2011 | Anderson et al. | |
| 2012/0034596 A1 | 2/2012 | Seidl et al. | |
| 2012/0040331 A1 | 2/2012 | Niazi | |
| 2013/0295551 A1 | 11/2013 | Eddington et al. | |

FOREIGN PATENT DOCUMENTS

| | | |
|---|---|---|
| WO | 2005/095576 | 10/2005 |
| WO | 2006/102890 | 10/2006 |
| WO | 2007/120619 | 10/2007 |
| WO | 2009/007692 | 1/2009 |
| WO | 2009/063190 | 5/2009 |
| WO | 2014/086984 | 6/2014 |
| WO | 20114/131091 | 9/2014 |

* cited by examiner

DEVICE AND SYSTEM FOR CREATING AND MAINTAINING A LOCALIZED ENVIRONMENT FOR A CELL CULTURE PLATE

BACKGROUND OF THE INVENTION

In vitro testing is often used in the earlier stages of pre-clinical testing to eliminate unsafe compounds prior to advancement to the later animal stages. For example, interconnected cellular networks of cardiomyocytes may be formed on a substrate for the testing of potential new heart therapies. Primary cardiomyocytes harvested from an animal, or animal or human stem-cell-derived cardiomyocytes, form interconnected cellular networks when cultured on a cell culture substrate. The individual cardiomyocytes within a network are connected through gap junctions that allow ions to flow from one cell to another. This electrical connection allows an electrical action potential, which is first generated by a pacemaker cell, to propagate from one cell to the next.

Formation of an electrical action potential starts with a buildup of charge across a cell membrane. This buildup occurs spontaneously in cardiac cells, and more frequently in pacemaker cardiomyocytes than non-pacemaking cardiomyocytes. When the transmembrane charge reaches a threshold value, ions rush into the first cell (the depolarization phase). This triggers an action potential, which is a sharp influx of additional ions into the cytoplasm. The gap junctions distributed across the cell membrane allow ions to flow into neighboring cells, enabling the spread of the action potential.

Molecular processes within the cell tie the electrical action potential to the physical contraction of the cardiomyocytes. The propagation of the cardiac action potential across an in vitro cellular network, and the resulting contraction, resembles the propagation and contraction observed within the human heart and thus is often referred to as a "beat". Many in vitro cardiomyocyte networks exhibit spontaneous beating, where each cardiac action potential propagation (and corresponding physical beat) is followed by a brief pause and then another cardiac action potential propagation and beat.

In vitro diagnostics allow researchers to analyze non-electrical properties of many types of cells, such as cell viability, density, and proliferation rates. However, electrically active cultures, such as cardiomyocytes, enable researchers to test additional properties related to electrical activity. For example, a cardiomyocyte culture may be assessed by the gap junction distribution, or degree of electrical connectivity between cells. This property may relate to the ability of a beat to be transmitted homogenously throughout a culture.

In another example, electrical measurements taken from a cardiomyocyte give researchers an indication of the cell health, quality, and level of maturity. For example, patch-clamp techniques provide measures of the action potential of an individual cell. A patch-clamp uses an electrode inserted into the cell membrane to measure transmembrane voltage. For a healthy cell, the cardiac action potential is initiated with a depolarization phase, where sodium rushes into the cell. The depolarization phase is followed by a plateau phase, dominated by the influx of calcium, where the cells remains depolarized, and ultimately a repolarization phase characterized by an outflux of potassium and a return to the starting transmembrane potential. Patch-clamp technologies can be used to detect abnormalities in the action potential within a single cell, which may point to functional problems. However, performing testing on individual cells is difficult and time-consuming. Furthermore, cardiomyocytes may behave differently when separated from their network, thus calling experimental results into question.

Other technologies, such as impedance measurement systems, can provide information about the physical beating of the cells, but do not reveal important functional information associated with the electrical action potential. Finally, optical imaging of the network electrophysiology can be performed using secondary voltage sensitive optical reporters. However, these protocols may be time consuming and cytotoxic, eliminating the ability to perform multiple experiments on the same culture.

Microelectrode arrays (MEAs) having a plurality of microelectrodes situated within each well enable researchers to measure signals from electrically active cells cultured on their surfaces. Herein, "microelectrode" and "electrode" will be used interchangeably. Cells are cultured across the array of electrodes within a well such that signals are detected from multiple electrically active cells, such as cardiomyocytes, simultaneously. These signals, called field potential signals, may change shape in response to the addition of a candidate compound to the cardiomyocyte culture. The changes may be used to evaluate the cardiac safety risk of a compound. Additionally, these measures may be used to develop and characterize new stem cell lines, to compare the electrophysiology of the cells to in vivo signals from native cardiomyocytes, and/or to evaluate in vitro models of disease.

In vitro electrophysiology culture systems having biosensors, MEAs, can provide important insights into networks of electrically active cells. MEA-based electrophysiology culture systems can be configured to concurrently monitor single-cell and network-level activity over extended periods of time and without affecting the cell culture under investigation. Since their instrumental role in the landmark discovery of spontaneous waves in a developing retina, the variety and scope of MEA-based electrophysiology applications has dramatically expanded. Recently, for example, MEA-based electrophysiology culture systems have been used to investigate the suppression of epileptic activity and in the study of novel plasticity mechanisms in cultured neural networks. Advances in cell culture preparations have similarly led to applications for MEA-based electrophysiology culture systems in the fields of drug screening, safety pharmacology, and biosensing.

Working with MEA-based systems requires physical access to the culture plate itself—for example, to setup, modify, or verify an ongoing experiment. One potential downside to physical access is the exposure of the culture plate and its contents to the ambient atmosphere. Typical ambient conditions are not ideal for cell growth and maintenance. For example, many cells prefer a Carbon dioxide ($CO_2$)-rich environment that does not exist in the ambient atmosphere. Therefore, a scientist may inadvertently jeopardize the health of the cells any time they interact with the culture plate. A need exists for a system that allows physical and/or chemical interaction with cells in an MEA-based system while maintaining the accuracy of results (e.g., by preventing beat-period drift) and also minimizing harm to the cells themselves.

In order to accomplish these and other goals, Applicant has created various devices and systems for creating and maintaining a localized environment for a cell culture plate. A localized environment may describe any environment in proximity to the cell culture plate, and may include, for example, temperature, $CO_2$ concentration, oxygen concentration, and so on.

SUMMARY

In one example embodiment, a system is provided for creating a localized environment for a cell culture plate. The system includes a dock shaped to receive the culture plate and a gas distribution device positioned on the dock. The gas distribution device includes a frame having a plurality of sides connected to form an opening, an internal channel within the frame for directing the gas mixture within the gas distribution device, an inlet port in fluid communication with the internal channel for receiving a gas mixture, and an aperture in fluid communication with the internal channel and configured to direct the gas mixture toward the opening.

The gas distribution device may include a plurality of apertures spaced apart from one another along the frame and configured to direct the gas mixture toward the opening. The gas mixture may comprise a $CO_2$ concentration of about 2-100%. The gas distribution device may provide a localized environment proximate the culture plate having a $CO_2$ concentration of about 0.5-20%. The plurality of apertures may be non-uniform in size, and/or the spacing between at least some of the plurality of apertures may be non-uniform.

The system may further include a heater arranged to provide heating energy to the culture plate. The heater may be used to support the culture plate within the dock. The system may also include a lid arranged to enclose the culture plate and at least a portion of the gas distribution device. The lid can include magnets configured to secure the lid to at least one of the gas distribution device or the dock. The lid can also include a gripping feature configured to mate with a robotic gripper. The dock and the gas distribution device respectively may include complementary magnets, and wherein the magnets are positioned to align the gas distribution device on the dock. Alternatively or in addition, the gas distribution device may mechanically engage the dock.

In some embodiments, a cross sectional area of the internal channel varies along a length of the channel of the gas distribution device. The system may also include a processor configured to determine a desired flow rate for the gas distribution device. The gas distribution device may allow a user to physically interact with the culture plate without disrupting the localized environment proximate the culture plate.

In another example embodiment, a method is provided for creating a localized environment for a cell culture plate. The method can include introducing a pressurized gas mixture into a gas distribution device, channeling the gas mixture within an internal channel of the gas distribution device, and expelling the gas mixture via a plurality of apertures in fluid communication with the internal channel, wherein the plurality of apertures are spaced apart from one another along the internal channel and are configured to direct the gas mixture at least partially toward a portion of the gas distribution device The method can also include providing a heater configured to provide heating energy to the culture plate and a dock shaped to receive the culture plate and the gas distribution device. The method may also include expelling a gas mixture having a $CO_2$ concentration of about 2-100% and/or forming a localized environment proximate the culture plate having a $CO_2$ concentration of about 0.5-20%.

DETAILED DESCRIPTION

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. The terminology used herein is for the purpose of describing particular aspects only and is not intended to be limiting.

Reference will be made to the drawings to describe various aspects of one or more implementations of the invention. The drawings are diagrammatic and schematic representations of one or more implementations, and are not limiting of the present disclosure. Moreover, while various drawings are provided at a scale that is considered functional for one or more implementations, the drawings are not necessarily drawn to scale for all contemplated implementations. The drawings thus represent an example scale, but no inference should be drawn from the drawings as to any required scale.

In the following description, numerous specific details are set forth in order to provide a thorough understanding described herein. It will be obvious, however, to one skilled in the art that the present disclosure may be practiced without these specific details. In other instances, well known aspects of electrophysiology culture systems, machining techniques, injection molding methodologies, and microelectromechanical systems (MEMS) have not been described in particular detail in order to avoid unnecessarily obscuring aspects of the disclosed implementations.

Figure 1:
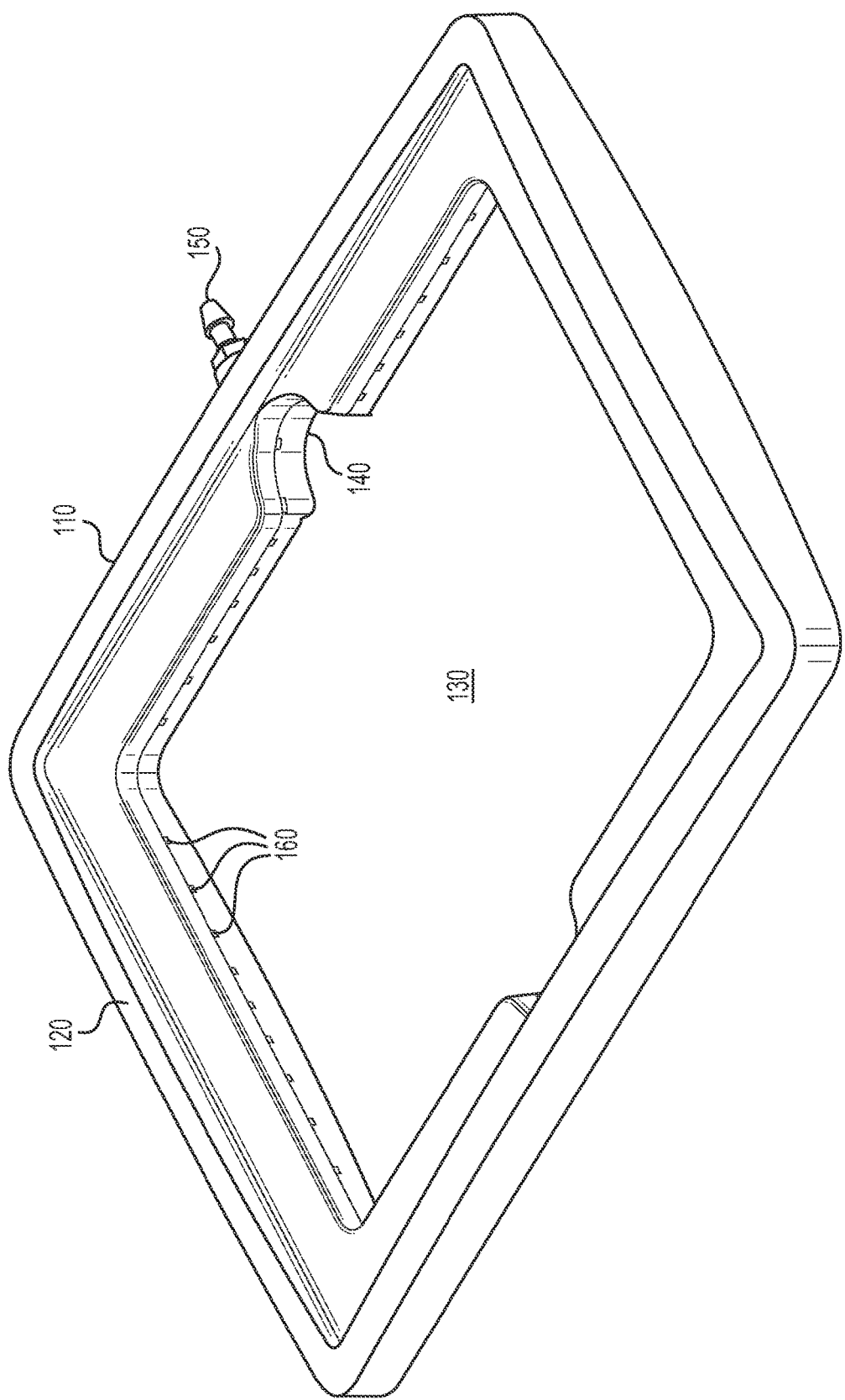
FIG. 1 is a schematic of an example embodiment of a gas distribution device for use with a culture plate.

Turning to FIG. 1, a gas distribution device 110 is depicted. Gas distribution device 110 includes a frame 120 having various sides connected to one another. In the embodiment of FIG. 1, the frame 120 includes four sides connected to one another forming an opening 130. Gas distribution device 110 may also include a frame 120 having fewer, or greater than, four sides. In addition, the sides of frame 120 are not necessarily connected to one another. For example, one side of the frame 120 may have a break with no material present. The frame 120 may also have non-uniform walls. For example, the frame 120 of gas distribution device 110 includes cutouts 140 on two sides of the frame 120. These cutouts may be useful in, for example, accessing an MEA plate underneath the gas distribution device 110. In any event, the central space between the portions of the frame 120 form opening 130.

Gas distribution device 110 is configured to receive and expel a gas mixture or any other type of fluid. Gas distribution device 110 can receive a gas mixture via inlet port 150, which is configured to attach to a hose or other device for providing the gas mixture. Inlet port 150 is in fluid communication with an internal channel (labeled 210 in FIG. 2) within the frame 120. By attaching a pressurized source of gas to inlet port 150, the gas is provided to the entire internal channel.

Also in fluid communication with the internal channel 210 is at least one aperture 160. As shown in FIG. 1, the gas distribution device 110 may have a plurality of apertures 160. The apertures 160 are formed within the frame 120 and connect to the internal channel 210. Any number of apertures 160 may be used according to the particular needs of the implementation. The size and/or shape of the apertures 160 may be varied as well, preferably in a manner that corresponds to the number of apertures 160 being used. For example, using a larger number of apertures 160 within the frame 120 may call for using smaller apertures 160, while using a smaller number of apertures 160 within the frame 120 may call for using larger apertures 160.

Apertures 160 may take any shape. For example, they may be round, square, rectangular, or triangular. In addition, apertures 160 may have a variety of sizes. In one example embodiment, each aperture 160 is approximately 0.5 mm×1.5 mm in size. However, apertures 160 may be smaller or larger. For example, apertures 160 may be approximately 0.25 mm×0.25 mm. As another example, apertures 160 may be approximately 100 mm×100 mm. Of course, apertures 160 may also be any sizes in between these example sizes. In some embodiments, aperture 160 may extend around a portion of the gas distribution device. In other embodiments aperture 160 may extend around the entire gas distribution device. Different sizes of apertures 160 may be mixed and matched to achieve the desired flow rate and flow pattern.

Figure 2:
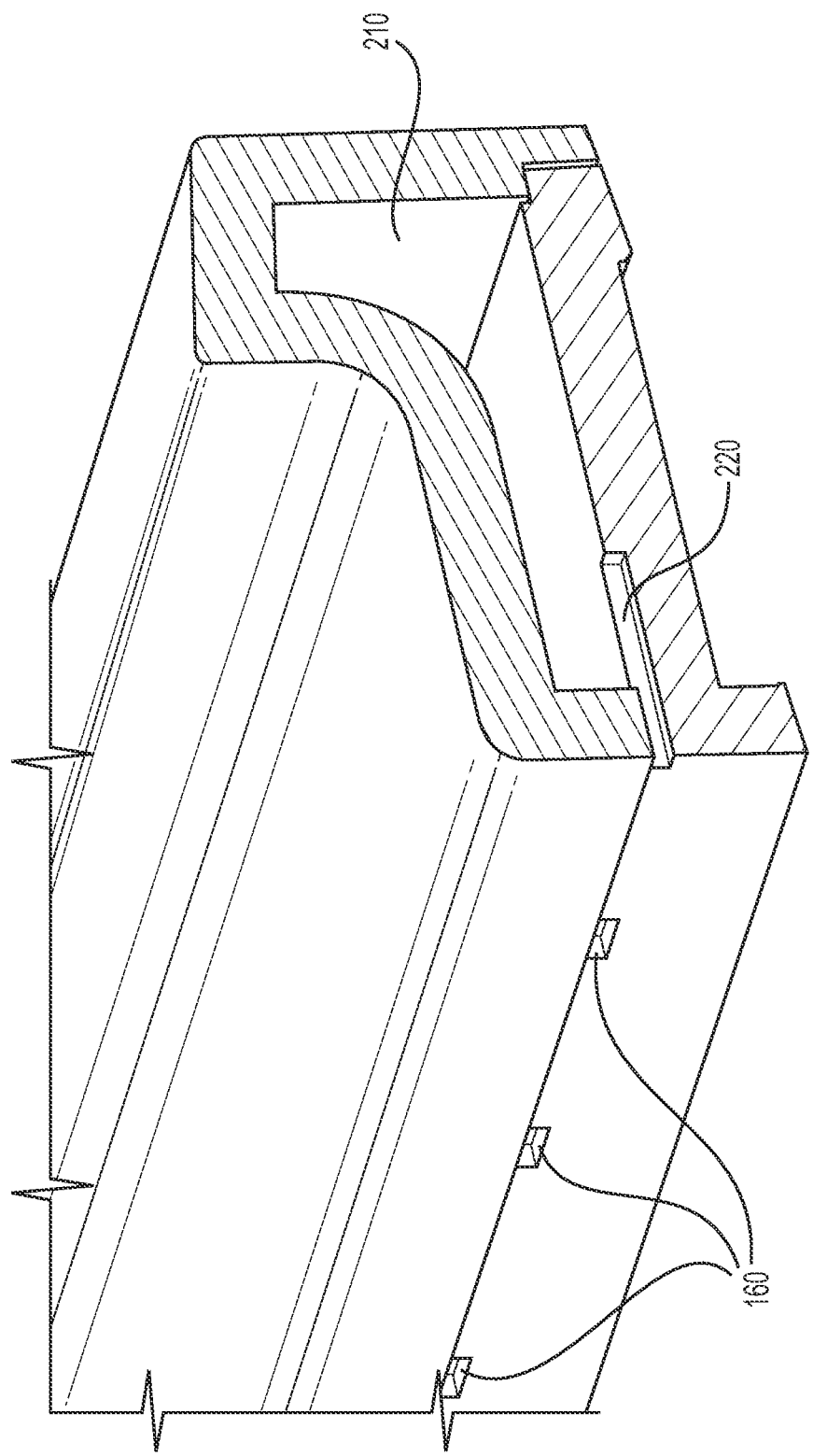
FIG. 2 is a cross sectional view of a portion of the example gas distribution device of FIG. 1.

As shown in FIG. 2, the apertures 160 may connect to the internal channel 210 via passages 220 within the frame 120. Passages 220 may be formed by, for example, providing a portion of the internal channel 210 that is cut out such that the gas mixture can reach the aperture 160. In FIG. 2, the passage 220 has a generally rectangular shape and is generally perpendicular to the direction of the internal channel 210. This orientation may be useful for directing gas flow in a direction that is generally perpendicular to the internal channel 210. In some embodiments, the passage 220 may be cut at an angle to the internal channel 210, which may provide gas flow at a similar angle. The sizes, orientations, and alignments of passages 220 may be mixed and match to achieve uniform flow properties across all apertures 160 and provide suitably even coverage across opening 130.

Figure 3:
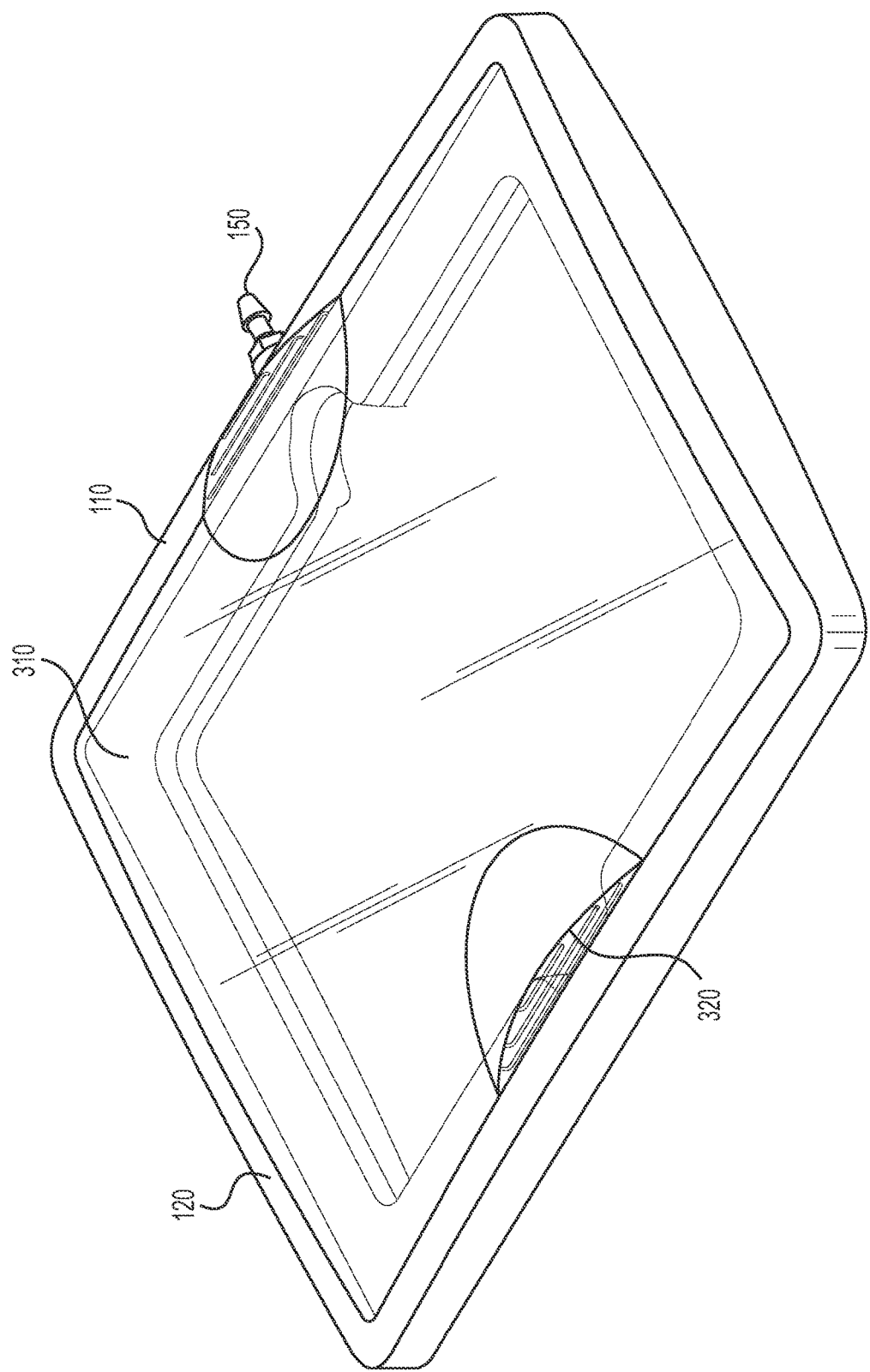
FIG. 3 is a schematic of an example embodiment of a gas distribution device having a lid affixed to the device.

FIG. 3 shows an embodiment of the gas distribution device 110 that includes a lid 310 that fits within the frame 120 of the device. The lid 310 may be used to temporarily cover a culture plate associated with the gas distribution device 110, allowing the localized environment to be maintained while providing a lower flow rate of the gas mixture. Use of the lid 310 provides additional containment of the environment by effectively eliminating a major exit path for the gas distributed via the gas distribution device 110. The lid 310 may be formed such that it is compatible with automated machines such as the Hamilton Microlab NIMBUS. For example, it may include one or more gripping features 320 configured to mate with a robotic gripper. As shown in FIG. 3, the gripping features 320 may comprise portions of the lid 310 arranged perpendicular to the plane defined by the frame 120. The gripping features 320 may also include ridges or other textual features that enhance the ability of a robotic gripper to grip the lid 310 securely. These features allow for an automated process that involves removing and/or installing the lid 310 on the gas distribution device 110.

Figure 4:
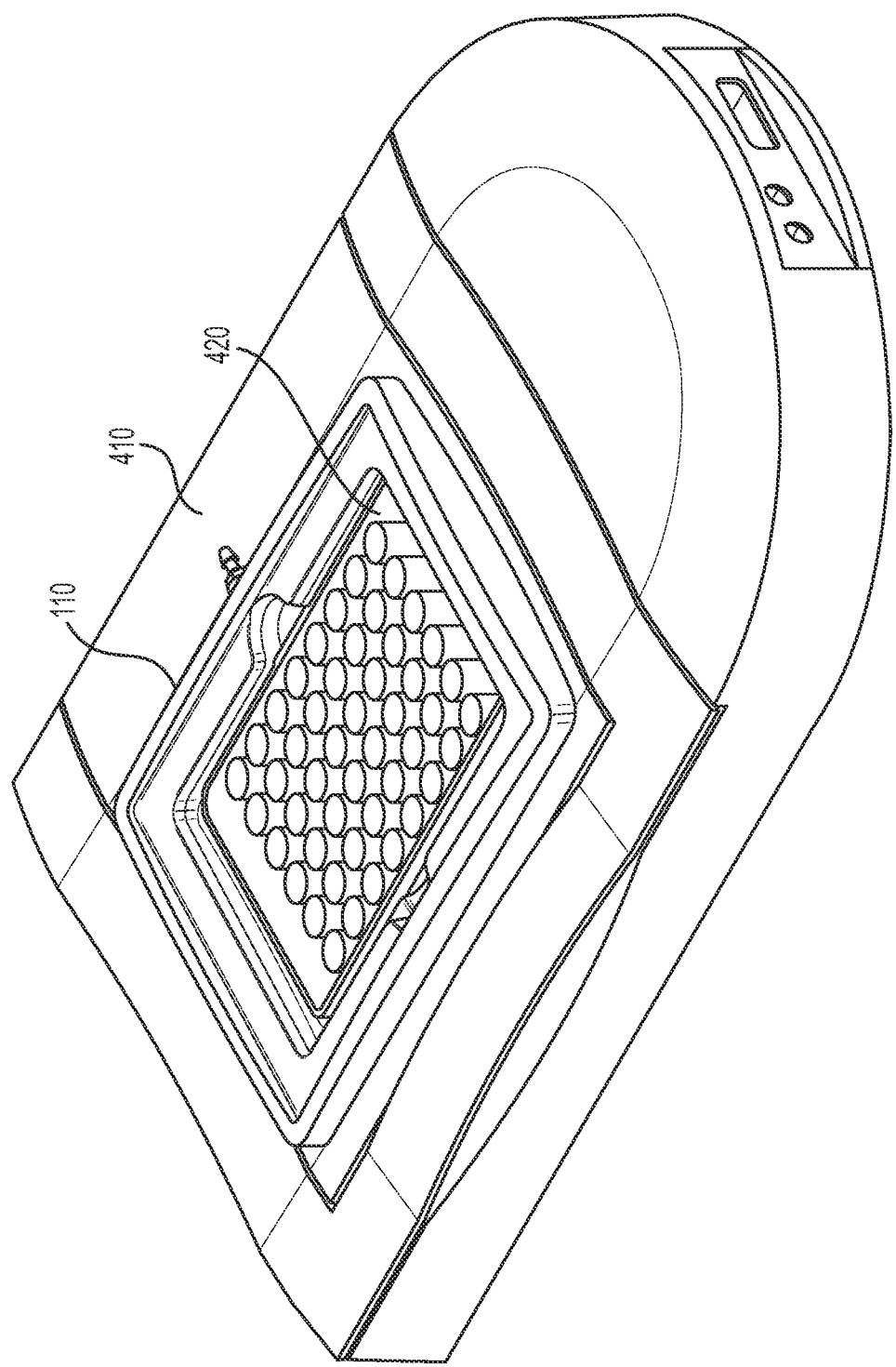
FIG. 4 is a schematic of an example embodiment of a gas distribution device arranged on a dock.

FIG. 4 illustrates an example embodiment of a dock 410 shaped to receive a culture plate 420, with a gas distribution device 110 installed on the dock 410. The dock 410 may also include a heater located underneath the culture plate 420 and potentially supporting the culture plate 420 from below.

Figure 5:
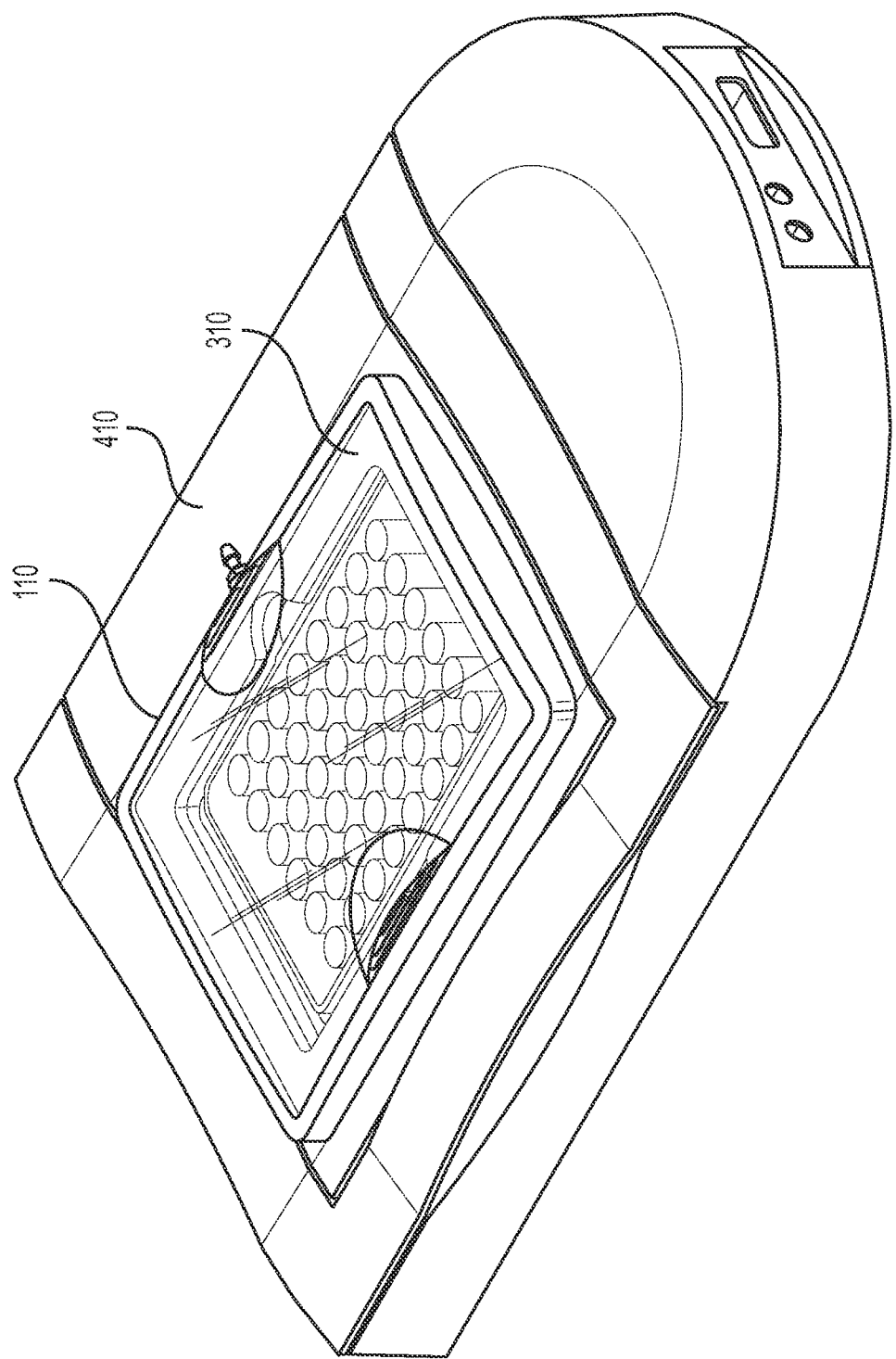
FIG. 5 is a schematic of an example embodiment of a gas distribution device having a lid affixed to the device, with the device arranged on a dock.

The gas distribution device 110 may be loosely positioned on the dock 410 or may be secured in some manner. For example, in some embodiments the gas distribution device 110 is mechanically attached to the dock via, for example, a press-fit connection, interlocking connection, or some other mechanical connection. In another embodiment, however, the gas distribution device 110 contains magnets corresponding to magnets with the dock 410. The corresponding sets of magnets can operate to position the gas distribution device 110 in the correct location and while also allowing for easy removal of the device. As shown in FIG. 5, a lid 310 may be used in conjunction with the gas distribution device 110 being attached to the dock 410.

When the dock 410 includes a culture plate 420 positioned therein and the gas distribution device 110 is attached and operable, the gas distribution device 110 is configured to provide a localized environment for the culture plate 420. The particular localized environment may vary depending on the particular needs to the medium within the culture plate. The term "localized environment" refers to the area proximate the culture plate 420 and its contents. For example, the localized environment of a culture plate may include the gas that is in direct contact with the culture plate 420 or its contents. As another example, the localized environment may include the area directly above the culture plate 420. As yet another example, the localized environment may include the opening 130 generally formed by frame 120 and shown in FIG. 1.

Generally speaking, the gas distribution device 110 can be configured to provide a localized environment providing an optimal concentration of any necessary element. For example, the gas distribution device 110 can be configured to provide a localized environment proximate the culture plate having a $CO_2$ concentration of about 0.5-20%. Higher or lower concentrations may be used, but a concentration of about 0.5-20% has been shown to improve cell activity and lifespan and increase the success rate of certain types of experiments.

In order to achieve and maintain the desired localized environment, the gas distribution device 110 may be configured to provide a gas mixture rich with whatever elements are desired for the culture being studied. For example, the gas distribution device 110 may provide a gas mixture having a $CO_2$ concentration of about 2-100%. The optimal $CO_2$ concentration of the gas mixture may vary based on many factors, such as: the flow rate of the gas mixture, the size/number/orientation of apertures, and whether a lid is being used. A lower flow rate may require a higher concentration of $CO_2$ in the gas mixture, while the use of a lid can lower the required concentration of $CO_2$. The concentration may be controlled and changed dynamically to meet the needs of the culture at issue. For example, a processor may be located within the dock 410 and may control the flow rate automatically.

Figure 6:
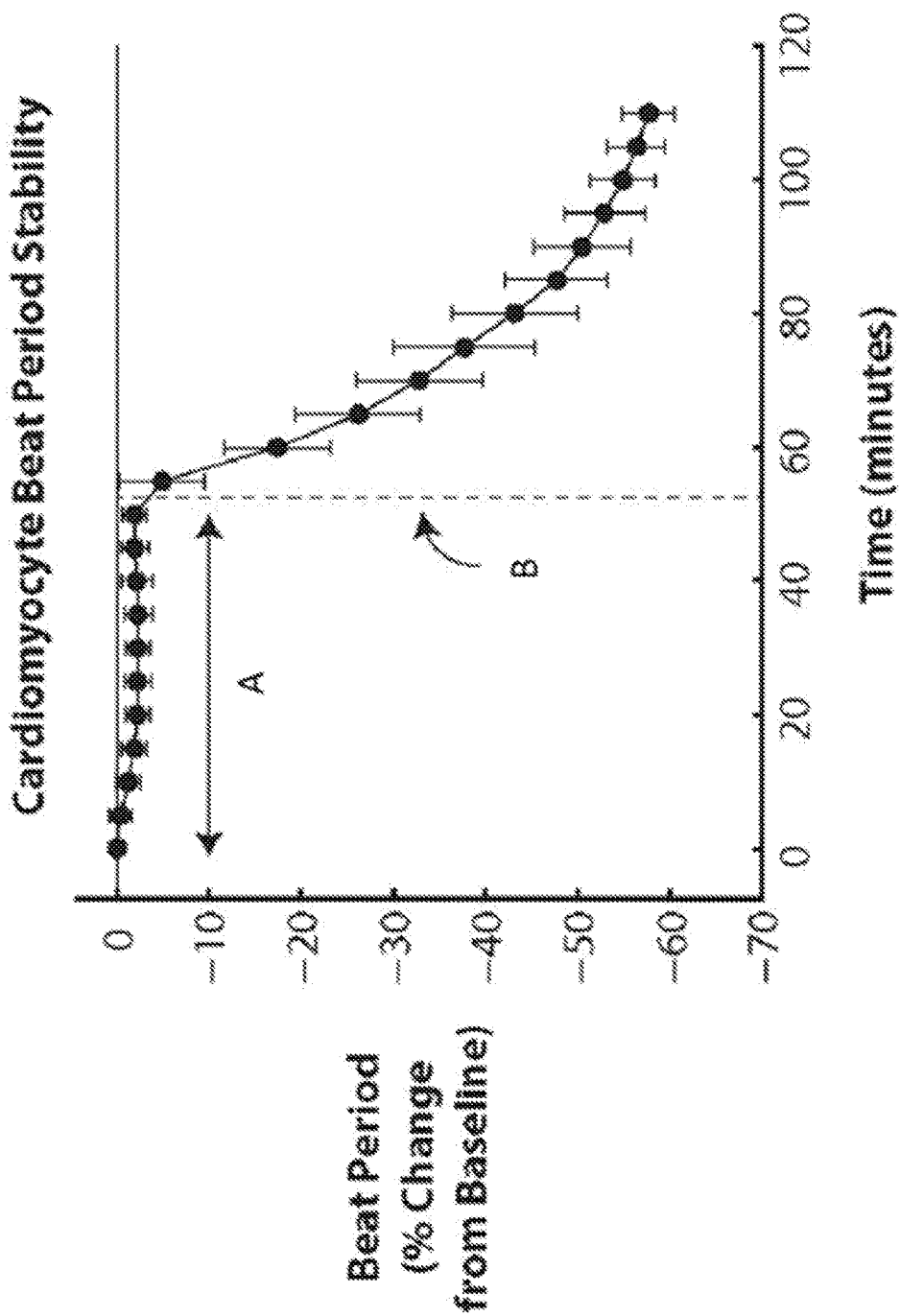
FIG. 6 is a graphical representation of cardiomyocyte beat period stability over time when utilizing an example embodiment of a gas distribution device for an initial time period.

Gas distribution device may be used in a variety of scenarios and circumstances. For example, FIG. 6 shows a graphical representation of cardiomyocyte beat period stability over time when utilizing an example embodiment of a gas distribution device 110 for an initial time period. Generally speaking, Cardiomyocytes are electrically active cells that are able to spontaneously contract. When cultured in vitro (e.g., on an MEA), cardiac cells form a functional beating syncytium, in which the entire culture contracts at the same time due to rapid conduction of electrical signals (cardiac action potentials) from cell to cell.

The field potential waveform captured by MEA recordings provides information on the depolarization, repolarization, and propagation of the cardiac action potential. For example, a depolarization spike on the field potential is due to current through the ion channels of the cell, and corresponds to the elements of the signal in a clinical Electro Cardio Graph (ECG) signal. From the depolarization spike, we also derive the onset of beat timing. The beat period is defined as the time interval between two consecutive beats. Although beat period is variable across cell types, any deviation from a culture's baseline may be indicative of poor culture health. Furthermore, cell sensitivity to compounds depends on beat period as well.

As a culture develops, the beat rate and beat period stabilize. Maintaining these stabilized rates depends, in part, on external factors such as pH and temperature. Temperature can be maintained through the use of heating elements integrated into the system or the MEA itself.

With respect to pH, careful control may be necessary to counteract pH changes caused by waste products of the cells. One way to control pH is to provide bicarbonate buffering tuned to a particular $CO_2$ level. In some embodiments a $CO_2$ level of about 5% may be used to maintain an appropriate pH. While other $CO_2$ levels may be used as well, FIG. 6 shows data based on 5% $CO_2$.

FIG. 6 shows a chart of the beat period, measured as a percent change from a baseline beat period, over a time period of about 110 minutes. During the stage labeled "A" a gas distribution device was utilized to provide $CO_2$-rich air to the cultures, thereby maintaining a localized environment. As shown in the graph, the beat period did not differ substantially from the baseline during stage A, fluctuating up to only approximately 3%. Stage B begins at the roughly 55-minute mark, and signifies the time when the $CO_2$ distribution ceased and the cultures were exposed to the ambient environment. The results show a sharp change in beat period stability, decreasing over 50% in about 30 minutes. This experiment demonstrates the utilization of an example embodiment of a device according to the present disclosure in a practical setting and shows excellent performance with respect to signal (in this case beat period) stability.

What is claimed is:

1. A system for creating a localized environment for a cell culture plate, comprising:
    a dock shaped to receive the cell culture plate; and
    a gas distribution device positioned on the dock, comprising:
        a frame comprising a plurality of sides connected to form an opening;
        an internal channel within the frame for directing a gas mixture within the gas distribution device, wherein the internal channel is disposed around the opening and is configured to direct the gas mixture around a periphery of the cell culture plate;
        an inlet port in fluid communication with the internal channel for receiving the gas mixture; and
        a plurality of apertures in fluid communication with the internal channel, wherein the plurality of apertures are spaced apart from one another along the frame and configured to direct the gas mixture toward the opening and around the periphery of the cell culture plate, and wherein the gas distribution device is configured to maintain a localized environment proximate the cell culture plate without disruption during physical interaction with the cell culture plate.

2. The system of claim 1, further comprising a heater configured to provide heating energy to the cell culture plate.

3. The system of claim 1, wherein the gas mixture comprises a $CO_2$ concentration of about 2-100%.

4. The system of claim 1, wherein the gas distribution device provides a localized environment proximate the cell culture plate having a $CO_2$ concentration of about 0.5-20%.

5. The system of claim 1, wherein at least some of the plurality of apertures are non-uniform in size.

6. The system of claim 1, wherein the spacing between at least some of the plurality of apertures are non-uniform.

7. The system of claim 1, wherein a cross sectional area of the internal channel varies along a length of the internal channel.

8. The system of claim 1, wherein the dock and the gas distribution device respectively comprise complementary magnets, and wherein the magnets are positioned to align the gas distribution device on the dock.

9. The system of claim 1, wherein the gas distribution device mechanically engages the dock.

10. The system of claim 1, further comprising a lid configured to enclose the cell culture plate and at least a portion of the gas distribution device.

11. The system of claim 10, wherein the lid comprises magnets configured to secure the lid to at least one of the gas distribution device or the dock.

12. The system of claim 10, wherein the lid comprises a gripping feature configured to mate with a robotic gripper.

13. The system of claim 1, further comprising a processor configured to determine a desired flow rate for the gas distribution device.

14. The system of claim 2, wherein the heater is configured to support the cell culture plate within the dock.

15. A method for creating a localized environment for a cell culture plate, comprising:
    introducing a pressurized gas mixture into a gas distribution device positioned on a dock shaped to receive the cell culture plate, the gas distribution device comprising a frame comprising a plurality of sides connected to form an opening, an internal channel within the frame for directing the gas mixture within the gas distribution device, an inlet port in fluid communication with the internal channel for receiving the gas mixture, and a plurality of apertures in fluid communication with the internal channel, wherein the internal channel is disposed around the opening and is configured to direct the gas mixture around a periphery of the cell culture plate;
    channeling the gas mixture within the internal channel of the gas distribution device;
    expelling the gas mixture via the plurality of apertures in fluid communication with the internal channel, wherein the plurality of apertures are spaced apart from one another along the internal channel and are configured to direct the gas mixture at least partially toward the opening of the gas distribution device and around the periphery of the cell culture plate; and
    maintaining, using the gas distribution device, a localized environment proximate the cell culture plate without disruption while a user physically interacts with the cell culture plate.

16. The method of claim 15, further comprising providing a heater configured to provide heating energy to the cell culture plate.

17. The method of claim 15, wherein expelling the gas mixture further comprises expelling a gas mixture having a $CO_2$ concentration of about 2-100%.

18. The method of claim 15, wherein expelling the gas mixture forms a localized environment proximate the cell culture plate having a $CO_2$ concentration of about 0.5-20%.

* * * * *

UNITED STATES PATENT AND TRADEMARK OFFICE
CERTIFICATE OF CORRECTION

PATENT NO. : 10,351,812 B2
APPLICATION NO. : 14/838575
DATED : July 16, 2019
INVENTOR(S) : Robert Dixon Grier, Jr. et al.

Page 1 of 1

It is certified that error appears in the above-identified patent and that said Letters Patent is hereby corrected as shown below:

In the Specification

In the first column, before the first paragraph at Line 5, please add the following paragraph:
STATEMENT REGARDING FEDERALLY FUNDED RESEARCH
This invention was made with government support under Grant no. R44NS062477 awarded by the National Institutes of Health. The government has certain rights in the invention.

Signed and Sealed this
Eighth Day of June, 2021

Drew Hirshfeld
*Performing the Functions and Duties of the
Under Secretary of Commerce for Intellectual Property and
Director of the United States Patent and Trademark Office*